(12) United States Patent
Sabir et al.

(10) Patent No.: US 8,562,626 B2
(45) Date of Patent: Oct. 22, 2013

(54) DEVICES FOR HARVESTING A SKIN GRAFT

(75) Inventors: Sameer Ahmed Sabir, Cambridge, MA (US); Andrew Ziegler, Arlington, MA (US)

(73) Assignee: Momelan Technologies, Inc., Cambridge, MA (US)

( * ) Notice: Subject to any disclaimer, the term of this patent is extended or adjusted under 35 U.S.C. 154(b) by 301 days.

(21) Appl. No.: 12/851,656

(22) Filed: Aug. 6, 2010

(65) Prior Publication Data

US 2012/0035599 A1 Feb. 9, 2012

(51) Int. Cl.
*A61B 18/18* (2006.01)
*A61B 17/50* (2006.01)

(52) U.S. Cl.
USPC ................ 606/132; 606/9; 606/131

(58) Field of Classification Search
USPC ............................................. 606/9
See application file for complete search history.

(56) References Cited

U.S. PATENT DOCUMENTS

| | | | |
|---|---|---|---|
| 2,379,574 A | 7/1945 | Goldthwait |
| 3,054,404 A | 9/1962 | Meek |
| 3,782,387 A | 1/1974 | Falabella |
| 4,666,447 A | 5/1987 | Smith |
| 4,773,418 A | 9/1988 | Hettich |
| 5,015,584 A | 5/1991 | Brysk |
| 5,441,490 A | 8/1995 | Svedman |
| 5,460,939 A | 10/1995 | Hansbrough et al. |
| 5,476,478 A | 12/1995 | Jackson |
| 5,489,304 A | 2/1996 | Orgill et al. |
| 5,545,222 A | 8/1996 | Bonutti |
| 5,571,098 A | 11/1996 | Domankevitz |
| 5,686,303 A | 11/1997 | Korman |
| 5,730,717 A | 3/1998 | Gelbfish |
| 5,759,193 A | 6/1998 | Burbank |
| 5,888,219 A | 3/1999 | Bonutti |
| 5,914,264 A | 6/1999 | Korman |
| 5,921,980 A | 7/1999 | Kirn |
| 6,056,738 A | 5/2000 | Marchitto |
| 6,063,094 A | 5/2000 | Rosenberg |
| 6,071,247 A | 6/2000 | Kennedy |
| 6,248,114 B1 | 6/2001 | Ysebaert |
| 6,254,580 B1 | 7/2001 | Svedman |
| 6,358,260 B1 | 3/2002 | Ross |
| 6,402,770 B1 | 6/2002 | Jessen |
| 6,623,498 B1 | 9/2003 | Ziemer |
| 6,800,282 B1 | 10/2004 | Thomson et al. |
| 6,860,904 B2 | 3/2005 | Bonutti |
| 7,078,582 B2 | 7/2006 | Stebbings |

(Continued)

FOREIGN PATENT DOCUMENTS

| | | |
|---|---|---|
| EP | 1614404 | 1/2006 |
| WO | 9211879 | 7/1992 |

(Continued)

OTHER PUBLICATIONS

Awad, Dermatol Surg, 34(9):1186-1193, 2008.

(Continued)

*Primary Examiner* — Armando Rodriguez
(74) *Attorney, Agent, or Firm* — Reza Mollaaghababa; Thomas J. Engellenner; Pepper Hamilton LLP

(57) ABSTRACT

The present invention generally relates to devices for harvesting a skin graft(s). The present invention provides a blister raising device integrated with a member for cutting the blister.

17 Claims, 5 Drawing Sheets

(56) References Cited

U.S. PATENT DOCUMENTS

| | | |
|---|---|---|
| 7,208,006 B2 | 4/2007 | Fleischmann |
| 7,244,444 B2 | 7/2007 | Bates |
| 7,540,875 B2 | 6/2009 | Jessen |
| 7,625,384 B2 | 12/2009 | Eriksson |
| 7,651,507 B2 | 1/2010 | Mishra |
| 7,666,134 B2 | 2/2010 | Eriksson |
| 7,666,192 B2 | 2/2010 | Seegert |
| 7,708,746 B2 | 5/2010 | Eriksson |
| 7,926,401 B2 | 4/2011 | Mishra |
| 8,109,187 B2 | 2/2012 | Mishra |
| 8,162,957 B2 | 4/2012 | Mishra |
| 8,187,285 B2 | 5/2012 | Eriksson |
| 2001/0029380 A1 | 10/2001 | Ysebaert |
| 2003/0009185 A1 | 1/2003 | Jessen |
| 2004/0097967 A1 | 5/2004 | Ignon |
| 2004/0172045 A1 | 9/2004 | Eriksson |
| 2004/0215217 A1 | 10/2004 | Banbury |
| 2004/0225309 A1 | 11/2004 | Eriksson |
| 2004/0230215 A1 | 11/2004 | Eriksson |
| 2004/0237744 A1 | 12/2004 | Lin |
| 2005/0038520 A1 | 2/2005 | Binette et al. |
| 2005/0101972 A1 | 5/2005 | Bhatavadekar |
| 2006/0141616 A1 | 6/2006 | Guu |
| 2006/0271070 A1 | 11/2006 | Eriksson |
| 2007/0183974 A1 | 8/2007 | Pearlman |
| 2010/0012311 A1 | 1/2010 | Colongo et al. |
| 2010/0042127 A1 | 2/2010 | Eriksson |
| 2010/0145360 A1 | 6/2010 | Eriksson |
| 2010/0152750 A1 | 6/2010 | Memar |
| 2011/0077664 A1 | 3/2011 | Schulz |
| 2011/0251602 A1 | 10/2011 | Anderson |
| 2011/0264115 A1 | 10/2011 | Asrani |
| 2012/0035599 A1 | 2/2012 | Sabir |
| 2012/0035618 A1 | 2/2012 | Sabir |
| 2012/0041430 A1 | 2/2012 | Anderson |
| 2012/0172894 A1 | 7/2012 | Sabir |
| 2012/0197267 A1 | 8/2012 | Sabir |
| 2012/0201793 A1 | 8/2012 | Bellomo |
| 2012/0271320 A1 | 10/2012 | Hall |
| 2013/0041385 A1 | 2/2013 | Giovannoli |

FOREIGN PATENT DOCUMENTS

| | | |
|---|---|---|
| WO | WO9528886 | 11/1995 |
| WO | 9618432 | 6/1996 |
| WO | 9633768 | 10/1996 |
| WO | 9720509 | 6/1997 |
| WO | 9816158 | 4/1998 |
| WO | 03020333 | 3/2003 |
| WO | 03039382 | 5/2003 |
| WO | 03049626 | 6/2003 |
| WO | 03049783 | 6/2003 |
| WO | 2004071313 | 8/2004 |
| WO | 2004075764 | 9/2004 |
| WO | 2004078032 | 9/2004 |
| WO | 2004105576 | 12/2004 |
| WO | 2005033273 | 4/2005 |
| WO | 2005046428 | 5/2005 |
| WO | 2007117488 | 10/2007 |
| WO | WO 2010/036788 | * 4/2010 |
| WO | WO2010036788 | 4/2010 |
| WO | 2011338326 | 3/2011 |
| WO | 2011059441 | 5/2011 |
| WO | 2011075676 | 6/2011 |
| WO | 2012019094 | 2/2012 |
| WO | 2012019095 | 2/2012 |
| WO | 2012019096 | 2/2012 |
| WO | 2012019098 | 2/2012 |
| WO | 2012102812 | 8/2012 |
| WO | 2012145504 | 10/2012 |

OTHER PUBLICATIONS

Kreis et al., Burns, 20(1):S39-S42, 1994.
Lari et al., Burns, 27:61-66, 2001.
Mulekar et al., Dermatol Surg 25(1):66-71, 2009.
Meek, Am J Surg., 96(4):557-558, 1958.
International Search Report and Written Opinion dated Dec. 16, 2011 for International Application No. PCT/US11/46737, 9 pages.
International Search Report and Written Opinion dated Dec. 23, 2011 for International Application No. PCT/US11/46739, 7 pages.
International Search Report and Written Opinion dated Dec. 16, 2011 for International Application No. PCT/US11/46738, 7 pages.
International Search Report and Written Opinion dated Dec. 6, 2011 for International Application No. PCT/US11/46741, 7 pages.

* cited by examiner

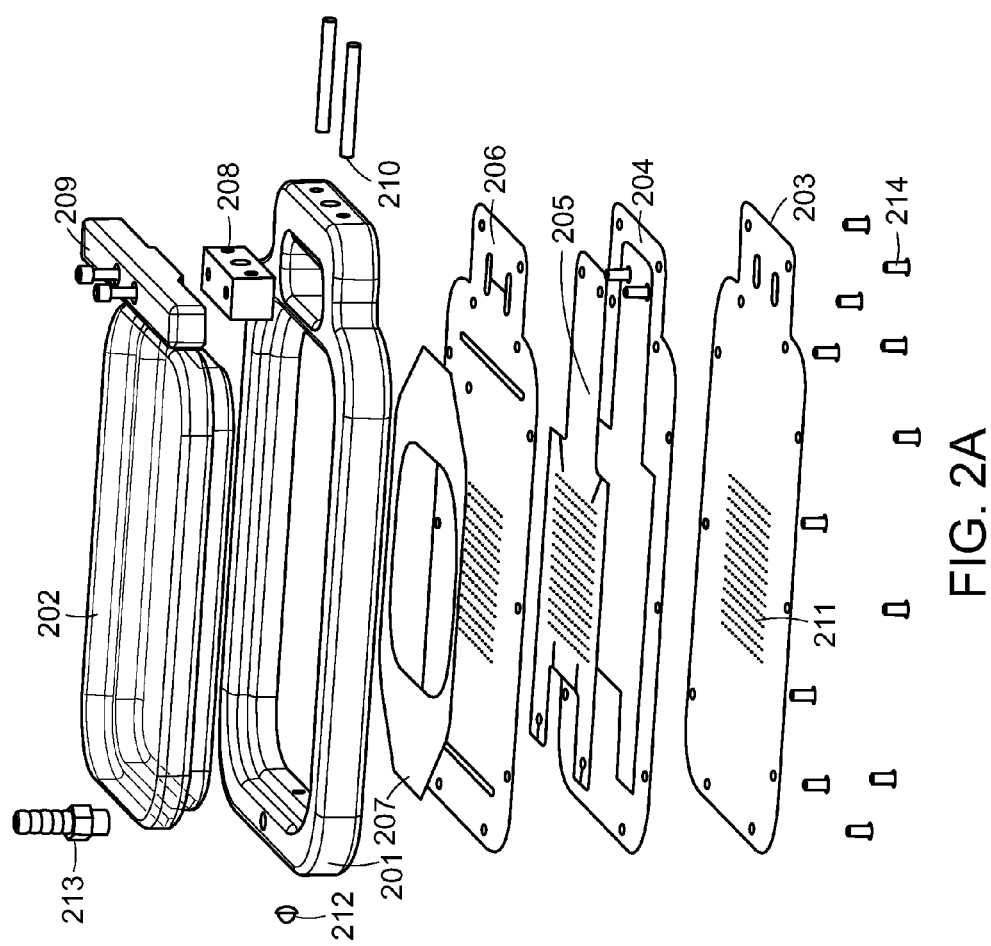
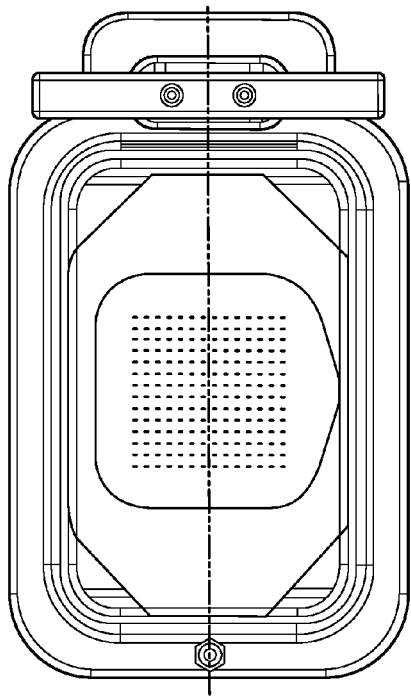
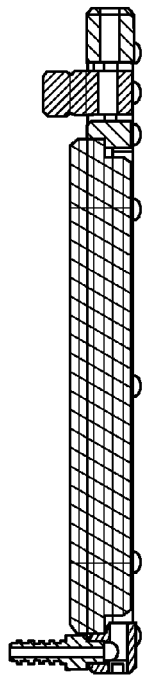
FIG. 2A
FIG. 2B
FIG. 2C

DEVICES FOR HARVESTING A SKIN GRAFT

FIELD OF THE INVENTION

The present invention generally relates to devices for harvesting a skin graft.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. Harvesting of a skin graft may be accomplished by many different techniques, and the technique used will depend on the type of graft to be harvested. A common technique to harvest a skin graft includes suction blistering. Suction blistering involves two devices, one device to raise a suction blister and a separate device to cut the blister. The need for two devices slows the graft harvesting process and requires that suction blistering be performed in a doctor's office. Further, the need for separate devices has prevented development of an automated system for producing a skin graft.

SUMMARY

The present invention provides a blister raising device integrated with a member for cutting the raised blister. The invention thus provides a single device that can raise a blister and cut the raised blister. Devices of the invention may raise and cut a plurality of blisters, or may raise and cut a single blister. The single blister may be used as a skin graft or may be further manipulated to produce an array of micrografts.

The mechanism for raising the blister may be any mechanism known in the art. In certain embodiments, a vacuum source for creating suction in the body is used. In other embodiments, a heat source for creating heat in the body is used. In certain embodiments, a combination of a vacuum source and a heating source is used. Devices of the invention may include a temperature regulator. In certain embodiments, the blister may be a fluid-filled blister (e.g. a suction blister). In other embodiments, the blister is not fluid-filled, i.e., raised skin having only air within. Device of the invention may be used to raise any type of blister (fluid-filled or not fluid-filled).

Cutting members for cutting raised blisters are known in the art. Devices of the invention may be integrated with any of those cutters, and the cutter used will depend on the type of graft(s) to be prepared. In certain embodiments, the cutter is a laser.

In certain embodiments, devices of the invention are configured to produce an epidermal graft, i.e., a graft that consists of substantially epidermal skin and does not include any substantial portion of the dermal layer.

BRIEF DESCRIPTION OF THE DRAWINGS

FIG. 2 panels A-C are schematics showing a device for generating and harvesting a plurality of micrografts. Panel A provides an exploded view of the device. Panel B provides a top view of the assembled device. Panel C provides a side view of the assembled device.

DETAILED DESCRIPTION

Figure 1:
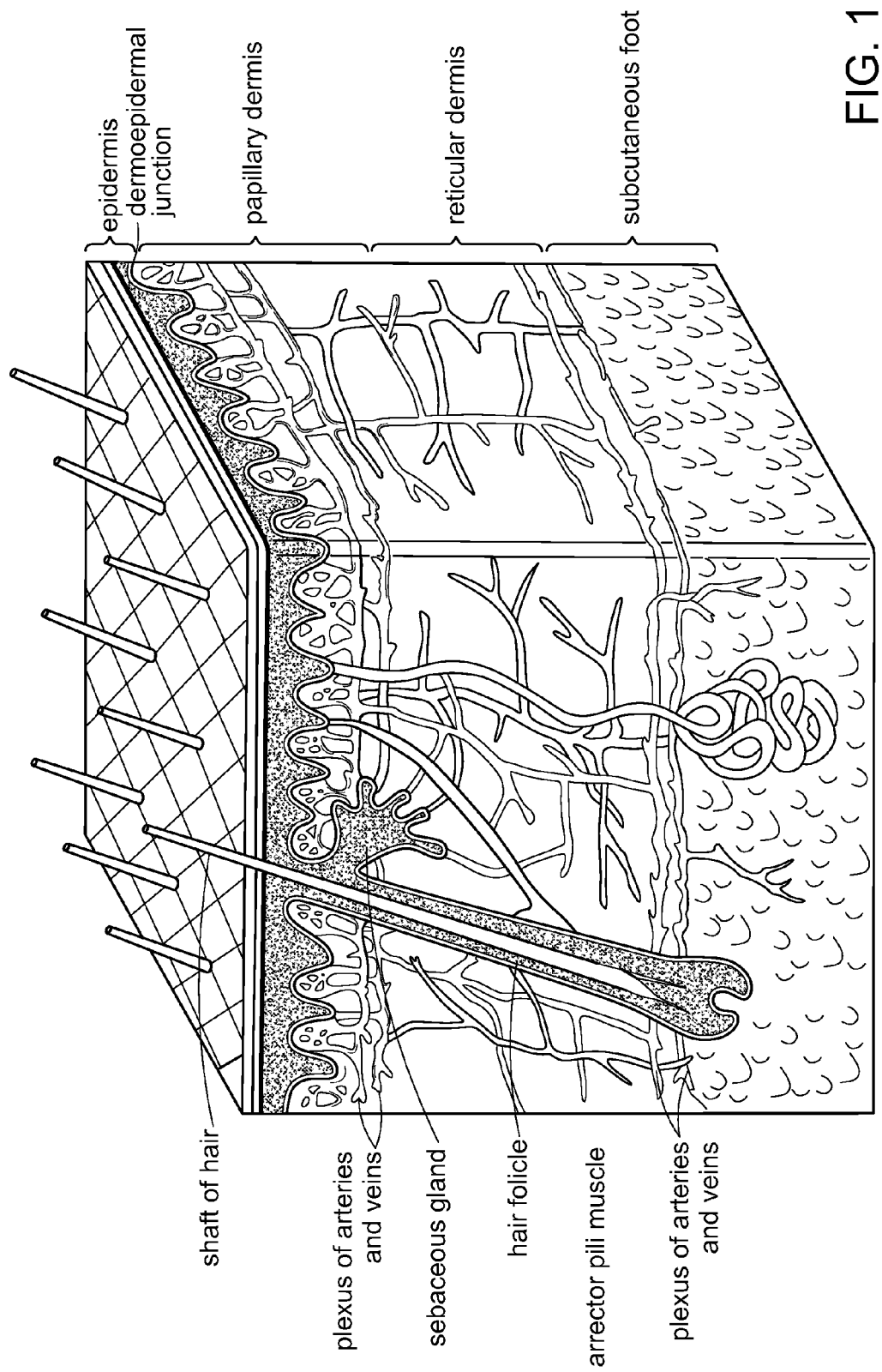
FIG. 1 provides a diagram showing the anatomy of skin.

The present invention generally relates to a single device that can raise a blister (e.g., a suction blister) and cut the raised blister, i.e., a blister raising device integrated with a cutting member. Such devices are useful for harvesting skin grafts.

In certain embodiments, a device as shown in FIG. 2 panels A-C is used to raise and cut a plurality of skin grafts. Device 200 includes a frame 201 and a lid 202. Fitted into the frame is a bottom plate 203, a cutter grid plate 204, a cutter plate 205, and a top plate 206. The bottom plate 203, the cutter plate 205, and the top plate 206, each include a hole array 211. Once assembled, the hole array 211 of each of plates 203, 205, and 206 are aligned. The size of the holes in the hole array will depend on the size of the graft needed, with larger holes being used to produce larger grafts. A first substrate 207 interacts with the top plate 206 and will receive the harvested grafts.

Device 200 further includes an actuation block 208, actuation bar 209, and actuation block guides 210. Actuation components 208, 209, and 210 control movement of the cutter plate 205. The frame 201 includes a vacuum stop 212 and the lid 202 includes a suction hole barb 213. Once assembled, the frame 201 and lid 202 are arranged such that the vacuum stop 212 and the suction hole barb 213 are aligned with each other (FIG. 2 panel B). A vacuum source is then connected to the device 200 such that negative pressure can be generated within the device. The device 200 can be held together by clamp screws 214. Device 200 may also include a heating element.

To produce and harvest the plurality of skin grafts, device 200 is placed on a donor site, such as an inner thigh of a patient. The vacuum source is turned on, producing negative pressure within device 200. The negative pressure causes the skin to be pulled toward lid 202, with a plurality of different portions of skin being pulled through each hole array 211 in each of plates 203, 205, and 206. Such action results in generation of many microblisters. Once the microblisters are raised, actuation components 208, 209, and 210 are engaged to move cutter plate 205. The movement of cutter plate 205 disrupts the alignment of the hole arrays 211 in each of plates 203, 205, and 206, and results in cutting of the microblisters.

The cut microblisters are captured on the first substrate 207 that is above top plate 206. In this manner, there is provided a spaced apart array of micrografts. The amount of negative pressure applied, the amount of time the vacuum is maintained, and/or the depth of the holes in plate 206 (i.e., the plate thickness) determine what type of graft will be harvested, e.g., epidermal graft, split thickness graft, or full thickness graft. Generally, each micrograft will have a lateral dimension of less than about 2 mm e.g., 100 to 2000 microns.

Another aspect of the invention provides a device for obtaining a single skin graft. Such devices of the invention include a hollow body having a distal end configured for placement on skin, a mechanism for raising a blister, and a cutter integrated in the body for cutting the blister produced on the skin.

Figure 3A:
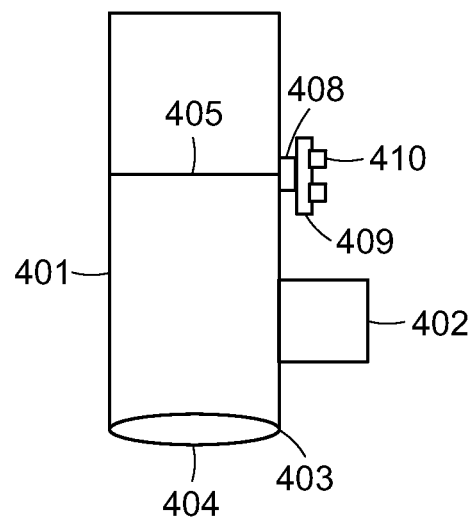
FIG. 3 panels A-B is a drawing showing a device of the invention for raising a suction blister.
Figure 3B:
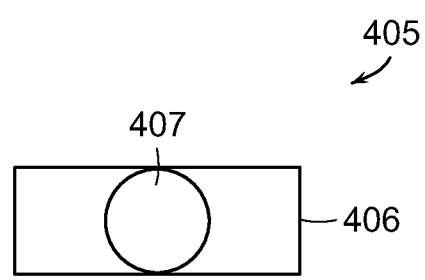
Figure 4A:
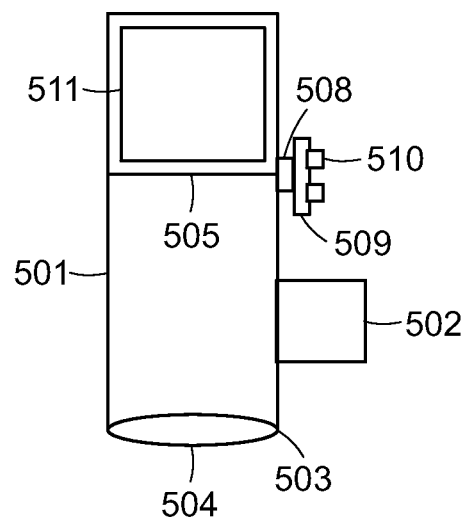
FIG. 4 panels A-D show different devices of the invention for raising a suction blister.
Figure 4B:
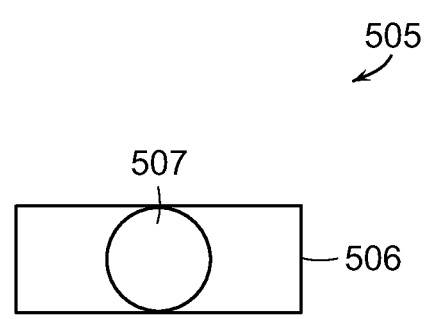
Figure 4C:
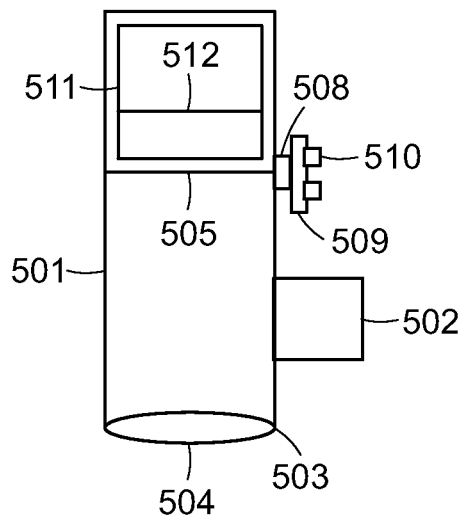
Figure 4D:
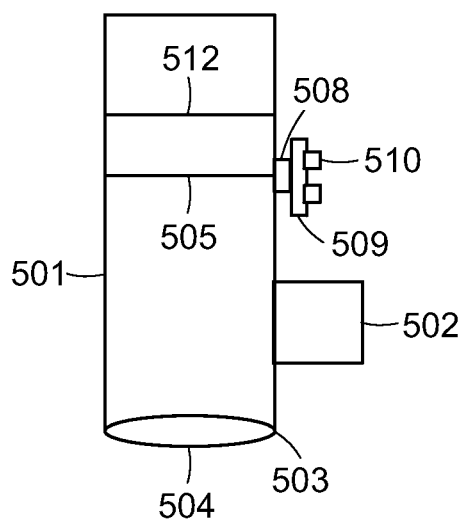

In certain embodiments, a device as shown in FIG. 3 panel A is used to obtain a skin graft. Device 400 includes a hollow body 401 and a mechanism for raising a blister 402. Hollow body 401 includes a distal end 403 that is configured for placement on the skin. Such a distal end may include an orifice plate 404. Orifice plate 404 determines the size and the shape of the blister or blisters that will be raised. Orifice plate 404 may be any shape or size and will depend on the blister to be raised. Generally, the diameter or lateral dimension of the blister may be from about 6 mm to about 12 mm, although larger or smaller blister sizes may be used.

The mechanism for raising a blister may be a vacuum component, a heating component, or a combination thereof. An exemplary heating component is a light source. In a particular embodiment, mechanism 402 is a combination of a vacuum component and a heating component.

The hollow body 401 further includes a cutter 405, which includes cutter plate 406 and a hole 407 (FIG. 3 panel B). Device 400 further includes an actuation block 408, actuation bar 409, and actuation block guides 410. Actuation components 408, 409, and 410 control movement of the cutter 405.

Blister formation is accomplished by attaching the distal end 403 of hollow body 401 to donor site of a patient, such as an inner thigh of a patient. Hook and loop fastener straps may be used to keep the device in place. The heating component of blister raising mechanism 402 provides a slight warming of orifice plate 404, which is in direct contact with the patient's skin surface. The application of a moderate negative pressure to the chamber interior from the vacuum component of blister raising mechanism 402, results in the patient's skin being gently drawn through the opening in orifice plate 404. The result is a blister or blisters, approximately the size of the opening in orifice plate 404. The produced blister may be fluid-filled or may not contain any fluid, i.e., a blister having air within. The skin and blister area is generally not damaged and patient discomfort is minimal.

The cutter 405 is positioned in hollow body 401 such that upon raising the blister, at least a portion of the blister protrudes through hole 407 in cutter plate 406. The actuation components 408, 409, and 410 are engaged to move cutter plate 406. The movement of cutter plate 406 disrupts the alignment of hole 407 with the other components of device 400, and results in cutting of the raised blister.

FIG. 4 panel A shows a device 500 that further includes a chamber 511 for capturing the cut blister. Chamber 511 is positioned in hollow body 501 and above cutter 505. Chamber 511 may be removable from device 500. Chamber 511 may include multiple configurations. For example, chamber 511 may include a retractable bottom. The bottom is in an open position when chamber 511 is inserted into hollow body 501. In the open position, chamber 511 is able to receive the cut blister. Once the cut blister is in chamber 511, the bottom of the chamber is closed, capturing the blister in chamber 511. Chamber 511 may then be removed from device 500.

In another embodiment, chamber 511 includes a substrate 512 (FIG. 4 panel C). In this embodiment, device 500 is configured such that substrate 512 is positioned in chamber 511 so that upon raising the blister, a portion of the blister contacts the substrate and becomes attached to the substrate. Cutter 505 then cuts the blister, and the cut blister becomes attached to the substrate 512 in chamber 511. Chamber 511 is then removed from device 500, and substrate 512 may be removed from chamber 511. In other devices, a vacuum, instead of a substrate, is used to hold the cut blister within the chamber.

In certain embodiments, device 500 does not use a chamber, rather a substrate 512 is directly integrated with device 500 in order to capture the cut blister (FIG. 4, panel D). Once captured, substrate 512 having an attached cut blister may be removed from device 500.

In certain embodiments, devices of the invention are configured to produce epidermal grafts. The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. FIG. 1 provides a diagram showing the anatomy of skin. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the 2 layers.

The dermis is a more complex structure. It is composed of 2 layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

In a graft, the characteristics of the donor site are more likely to be maintained after grafting to a recipient site as a function of the thickness of the dermal component of the graft. However, thicker grafts require more favorable conditions for survival due to the requirement for increased revascularization. It has been discovered, however, that a substantially epidermal graft according to the invention is more likely to adapt to the characteristics of the recipient site.

An epidermal graft refers to a graft that consists of substantially epidermal skin and does not include any substantial portion of the dermal layer. A split thickness graft refers to a graft that includes sheets of superficial (epithelial) and some deep layers (dermal) of skin. A full-thickness graft refers to a graft that includes all of the layers of the skin including blood vessels.

Devices of the invention may be used to harvest a skin graft(s) for repair of numerous different types of skin damage. For example, harvested grafts may be used to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

In particular embodiments, the skin graft(s) are used to treat vitiligo. Vitiligo is a chronic disorder that causes depigmentation of patches of skin. It occurs when melanocytes, the cells responsible for skin pigmentation, die or are unable to function. Although patches are initially small, they often enlarge and change shape. When skin lesions occur, they are most prominent on the face, hands and wrists. Some lesions have hyper-pigmentation around the edges. Depigmentation is particularly noticeable around body orifices, such as the mouth, eyes, nostrils, genitalia and umbilicus.

Vitiligo is generally classified into two categories, non-segmental vitiligo and Segmental vitiligo. In non-segmental vitiligo (NSV), there is usually some form of symmetry in the location of the patches of depigmentation. New patches also appear over time and can be generalized over large portions of the body or localized to a particular area. Vitiligo where little pigmented skin remains is referred to as vitiligo universalis. Non-segmental vitiligo can come about at any age, unlike segmental vitiligo which is far more prevalent in teenage years.

Segmental vitiligo (SV) differs in appearance, aetiology and prevalence from associated illnesses. Its treatment is different from that of non-segmental vitiligo. It tends to affect areas of skin that are associated with dorsal roots from the spine. It spreads much more rapidly than non-segmental vitiligo and, without treatment, it is much more stable/static in course and not associated with auto-immune diseases.

To treat vitiligo, an autograft is provided to the site of depigmented skin. The graft includes melanocytes, and thus upon the recipient site accepting the graft, the graft will produce pigmented skin at the recipient site. A donor site of pigmented skin is aseptically cleaned prior to harvesting of a skin graft. Standard methods are used to clean the donor site. A typical donor site is an inner thigh, but any area of pigmented skin may be used.

After cleaning, a skin grafted is harvested using devices of the invention. Devices described herein raise and cut a blister(s), such as a suction blister. The area of depigmented skin (i.e., the recipient site), is prepared through aseptic cleaning and dermabrasion. The graft(s) is applied to the dermabraded recipient site. The donor site and the recipient site are dressed and wound care is provided.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for obtaining a skin graft, the device comprising:
   a hollow body, the body having a distal end configured for placement on skin, the body further adapted to be coupled to a vacuum source, such that a negative pressure can be generated within the device when the body is placed on a donor's skin to raise at least one blister; and
   a harvesting member integrated in said body for cutting said blister produced on said skin, the harvesting member comprising a bottom plate, a cutter plate and a top plate, each plate having at least one hole, said holes forming an aligned hole array such that a raised skin blister can be pulled through the holes in each of the plates by the negative pressure, the harvesting member further comprising an actuator for moving the cutter plate to disrupt the alignment of holes and cut the raised blister.

2. The device according to claim 1, wherein the device further comprises a mechanism selected from the group consisting of a vacuum source for creating suction in said body; a heat source for generating heat in either a patient's body or the body of hollow body of the device; and a combination thereof.

3. The device according to claim 2, wherein the heat source is a light source.

4. The device according to claim 2, further comprising a temperature regulator.

5. The device according to claim 1, further comprising a chamber positioned above the harvesting mechanism.

6. The device according to claim 5, wherein the chamber comprises a substrate.

7. The device according to claim 1, further comprising a substrate positioned above the harvesting member.

8. The device according to claim 5, wherein the chamber is removable.

9. The device according to claim 5, wherein the chamber is disposable.

10. The device according to claim 5, wherein the chamber is reusable.

11. A device for obtaining a skin graft, the device comprising
   a hollow body having a distal end configured for placement on skin the body further adapted to be coupled to a vacuum source, such that negative pressure can be generated within the device when the body is placed on a donor's skin to raise at least one blister;
   a harvesting member integrated in said body for cutting said blister produced on said skin, the harvesting member comprising a bottom plate, a cutter plate and a top plate, each plate having at least one hole, said holes forming an aligned hole array such that a raised skin blister can be pulled through the holes in each of the plates by the negative pressure, the harvesting member further comprising an actuator for moving the cutter plate to disrupt the alignment of holes and cut the raised blister; and
   a chamber connected to the body, wherein the device is configured such that upon cutting of the blister, the cut portion of skin enters the chamber and is retained in the chamber.

12. The device according to claim 11, wherein the chamber is removable.

13. The device according to claim 11, wherein the chamber is disposable.

14. The device according to claim 11, wherein the chamber is reusable.

15. The device according to claim 11, wherein the chamber comprises a substrate.

16. A device for obtaining a skin graft, the device comprising a hollow body having a distal end configured for placement on skin, the body further adapted to be coupled to a vacuum source, such that negative pressure can be generated within the device when the body is placed on a donor's skin to raise at least one blister;

a harvesting member integrated in said body for cutting said blister produced on said skin, the harvesting member comprising a bottom plate, a cutter plate and a top plate, each plate having at least one hole, said holes forming an aligned hole array such that a raised skin blister can be pulled through the holes in each of the plates by the negative pressure, the harvesting member further comprising an actuator for moving the cutter plate to disrupt the alignment of holes and cut the raised blister; and a substrate removably connected to the body, wherein the device is configured such that upon cutting of the blister, the cut portion of skin is attached to the substrate.

17. The device according to claim 16, wherein the substrate comprises an adhesive.

* * * * *